US011033256B2

(12) United States Patent
Zammataro et al.

(10) Patent No.: US 11,033,256 B2
(45) Date of Patent: Jun. 15, 2021

(54) LINKAGE ASSEMBLY FOR REUSABLE SURGICAL HANDLE ASSEMBLIES

(71) Applicant: Covidien LP, Mansfield, MA (US)

(72) Inventors: Thomas A. Zammataro, Hamden, CT (US); Brian J. Creston, West Haven, CT (US); Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 84 days.

(21) Appl. No.: 16/433,109

(22) Filed: Jun. 6, 2019

(65) Prior Publication Data

US 2020/0046328 A1 Feb. 13, 2020

Related U.S. Application Data

(60) Provisional application No. 62/718,027, filed on Aug. 13, 2018.

(51) Int. Cl.
 *A61B 17/00* (2006.01)
(52) U.S. Cl.
 CPC ...... *A61B 17/00* (2013.01); *A61B 2017/0042* (2013.01); *A61B 2017/0046* (2013.01); *A61B 2017/00367* (2013.01)
(58) Field of Classification Search
 None
 See application file for complete search history.

(56) References Cited

U.S. PATENT DOCUMENTS

| | | | |
|---|---|---|---|
| 3,120,230 A | 2/1964 | Skold | |
| 3,638,847 A | 2/1972 | Noiles et al. | |
| 4,226,242 A | 10/1980 | Jarvik | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |

(Continued)

FOREIGN PATENT DOCUMENTS

| | | |
|---|---|---|
| CN | 103251441 A | 8/2013 |
| EP | 0732078 A2 | 9/1996 |

(Continued)

OTHER PUBLICATIONS

International Search Report corresponding to Int'l Patent Appln. PCT/US2018/050316 dated Dec. 31, 2018.

(Continued)

*Primary Examiner* — Brian T Gedeon
(74) *Attorney, Agent, or Firm* — Carter, DeLuca & Farrell LLP

(57) ABSTRACT

A handle assembly for actuating an end effector is provided. The handle assembly includes an actuation mechanism with a linkage assembly configured to maximize the output force. The linkage assembly includes first, second, and third linkage members operably disposed between a trigger and a drive member.

18 Claims, 8 Drawing Sheets

(56) References Cited

U.S. PATENT DOCUMENTS

| | | |
|---|---|---|
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,336,458 A | 8/1994 | Hutchison et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |

(56) References Cited

U.S. PATENT DOCUMENTS

| | | |
|---|---|---|
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,824,547 A | 10/1998 | Hashino et al. |
| 5,824,548 A | 10/1998 | Hearn |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,044,971 A | 4/2000 | Esposito et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |

(56) References Cited

U.S. PATENT DOCUMENTS

| | | |
|---|---|---|
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,446 B2 | 12/2005 | Hommann et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,696 B2 | 1/2008 | Wilson, Jr. et al. |
| 7,585,304 B2 | 9/2009 | Hughett |
| 7,819,886 B2 | 10/2010 | Whitfield et al. |
| 7,905,890 B2 | 3/2011 | Whitfield et al. |
| 8,048,088 B2 | 11/2011 | Green et al. |
| 8,075,571 B2 | 12/2011 | Vitali et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,328,822 B2 | 12/2012 | Huitema et al. |
| 8,403,138 B2 | 3/2013 | Weisshaupt et al. |
| 8,419,752 B2 | 4/2013 | Sorrentino et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,753,356 B2 | 6/2014 | Vitali et al. |
| 8,821,516 B2 | 9/2014 | Huitema |
| 8,894,665 B2 | 11/2014 | Sorrentino et al. |
| 8,915,930 B2 | 12/2014 | Huitema et al. |
| 9,282,972 B1 | 3/2016 | Patel et al. |
| 9,445,810 B2 | 9/2016 | Cappola |
| 9,526,565 B2 | 12/2016 | Strobl |
| 9,717,504 B2 | 8/2017 | Huitema |
| 9,782,181 B2 | 10/2017 | Vitali et al. |
| 10,136,939 B2 | 11/2018 | Minnelli et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |

(56) References Cited

U.S. PATENT DOCUMENTS

| | | |
|---|---|---|
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2009/0204115 A1 | 8/2009 | Dees, Jr. et al. |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2010/0089970 A1 | 4/2010 | Smith et al. |
| 2010/0331862 A1 | 12/2010 | Monassevitch et al. |
| 2011/0087220 A1 | 4/2011 | Felder et al. |
| 2011/0087268 A1 | 4/2011 | Livneh |
| 2012/0022526 A1 | 1/2012 | Aldridge et al. |
| 2013/0041379 A1 | 2/2013 | Bodor et al. |
| 2013/0325057 A1 | 12/2013 | Larson et al. |
| 2014/0188159 A1 | 7/2014 | Steege |
| 2014/0276736 A1* | 9/2014 | Worrell ............ A61B 18/1445 606/33 |
| 2014/0371728 A1 | 12/2014 | Vaughn |
| 2015/0201953 A1 | 7/2015 | Strobl et al. |
| 2015/0265282 A1 | 9/2015 | Miles et al. |
| 2015/0313452 A1 | 11/2015 | Nasser et al. |
| 2015/0314451 A1 | 11/2015 | Nixon |
| 2016/0004956 A1 | 1/2016 | Reynolds et al. |
| 2017/0202567 A1 | 7/2017 | Griffiths et al. |

(56) References Cited

U.S. PATENT DOCUMENTS

| | | |
|---|---|---|
| 2017/0245921 A1 | 8/2017 | Joseph et al. |
| 2017/0252042 A1 | 9/2017 | Kethman et al. |
| 2017/0290587 A1 | 10/2017 | Schober et al. |
| 2018/0021041 A1 | 1/2018 | Zhang et al. |
| 2018/0263624 A1 | 9/2018 | Malkowski et al. |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1609427 A1 | 12/2005 |
| EP | 1712191 A2 | 10/2006 |
| EP | 1813199 A1 | 8/2007 |
| EP | 1908423 A2 | 4/2008 |
| EP | 1913881 A1 | 4/2008 |
| EP | 3132756 A1 | 2/2017 |
| JP | 2011186812 A | 9/2011 |
| JP | 2013166982 A | 8/2013 |
| WO | 9003763 A1 | 4/1990 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2008118928 A2 | 10/2008 |
| WO | 2008127968 A2 | 10/2008 |
| WO | 2017084000 A1 | 5/2017 |
| WO | 2017146138 A1 | 8/2017 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.

* cited by examiner

LINKAGE ASSEMBLY FOR REUSABLE SURGICAL HANDLE ASSEMBLIES

CROSS-REFERENCE TO RELATED APPLICATION

This application claims the benefit of and priority to U.S. Provisional Patent Application No. 62/718,027 filed Aug. 13, 2018, the entire disclosure of which is incorporated by reference herein.

BACKGROUND

Technical Field

The present disclosure relates to handle assemblies for surgical instruments. More particularly, the present disclosure relates to linkage assemblies for reusable surgical handle assemblies.

Description of Related Art

Reusable handle assemblies are known in the medical art and are used for a number of distinct and useful surgical procedures. In the case of a laparoscopic surgical procedure, access to the interior of an abdomen is achieved through narrow tubes or cannulas that are releasably secured to the reusable handles inserted through a small entrance incision in the skin. Minimally invasive procedures performed elsewhere in the body are often generally referred to as endoscopic procedures.

Generally, handle assemblies are configured to translate a rotational input force into a linear output force. It would be beneficial to have a handle assembly that includes a linkage assembly that translates a rotational input force into a linear output force necessary for performing a procedure, while maximizing a mechanical advantage of the linkage assembly.

SUMMARY

A handle assembly for actuating an end effector is provided. According to an aspect of the present disclosure, the handle assembly includes a housing defining a longitudinal axis; a trigger operably coupled to the housing and movable to cause actuation of the handle assembly; a drive member movable within the housing from an initial position to an advanced position in response to actuation of the trigger; and a linkage assembly operably disposed between the trigger and the drive member to move the drive member from the initial position to the advanced position. The linkage assembly including first, second, and third linkage members, the first linkage member being pivotally secured to the trigger on a first end and to first ends of the second and third linkage members on a second end, the second linkage member being pivotally secured to the drive member on a second end, and the third linkage member being pivotally secured to the housing on a second end.

The first and third linkage members each may include a pair of linkage members.

A first end of the first linkage member may be pivotally secured to the trigger by a first pivot pin.

The housing may define a track and the first pivot pin extends within the track.

The housing may include a body portion and a trigger portion.

The handle assembly may further include a friction reducing mechanism operably disposed within the housing relative to the drive member.

The friction reducing mechanism may include first and second bearing assemblies, each of the bearing assemblies including a sleeve rotatably disposed within the housing and configured to facilitate movement of the drive member.

The first bearing assembly may be positioned such that a longitudinal axis of the second linkage member is tangent to the first bearing sleeve when the linkage assembly is in an initial condition.

The second bearing assembly may be positioned such that the longitudinal axis of the second linkage member is tangent to the second bearing sleeve when the linkage assembly is in a fully-actuated condition.

The first bearing assembly may include a first pivot pin and the second bearing assembly includes a second pivot pin, the first and second bearing sleeves being rotatably supported about the respective first and second pivot pins.

The housing may include a pivot post and the friction reducing mechanism includes a bearing sleeve, the bearing sleeve being received about the pivot post between the pivot post and the trigger to reduce friction between the housing and the trigger during actuation of the handle assembly.

The second and third linkage members may define a first angle therebetween when the drive member is in the initial position. The first angle may be less than ninety degrees.

The second and third linkage members may define a second angle therebetween when the drive member is in the advanced position. The second angle may be greater than ninety degrees.

The handle assembly may further include a feedback mechanism disposed within the housing to indicate when the drive member attains the advanced position.

BRIEF DESCRIPTION OF THE DRAWINGS

Aspects and features of the present disclosure are described in detail with reference to the drawing figures wherein like reference numerals identify similar or identical structural elements and.

DETAILED DESCRIPTION

Figure 1:
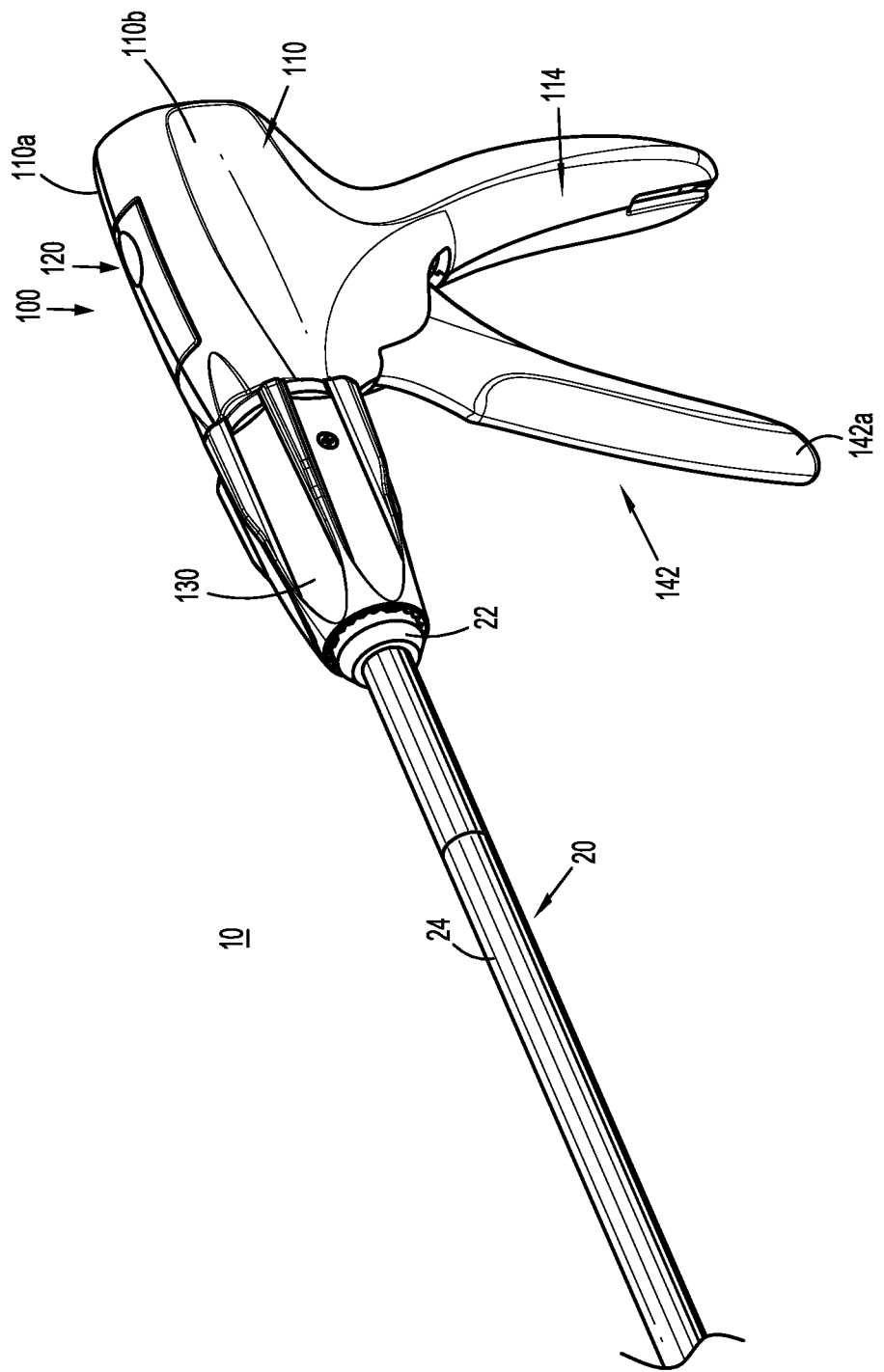
FIG. 1 is a front, perspective view of a surgical instrument according to an embodiment of the present disclosure including a handle assembly having an elongated assembly engaged therewith.

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is farther away from the user. Further, to the extent consistent, any or all of the aspects and features detailed herein may be used in conjunction with any or all of the other aspects and features detailed herein.

The present disclosure provides a linkage assembly for handle assemblies of surgical instruments. Although detailed herein as incorporated into handle assemblies for surgical instruments, such as clip appliers, the linkage assembly of the present disclosure may be incorporated into any suitable surgical instrument.

Figure 2:
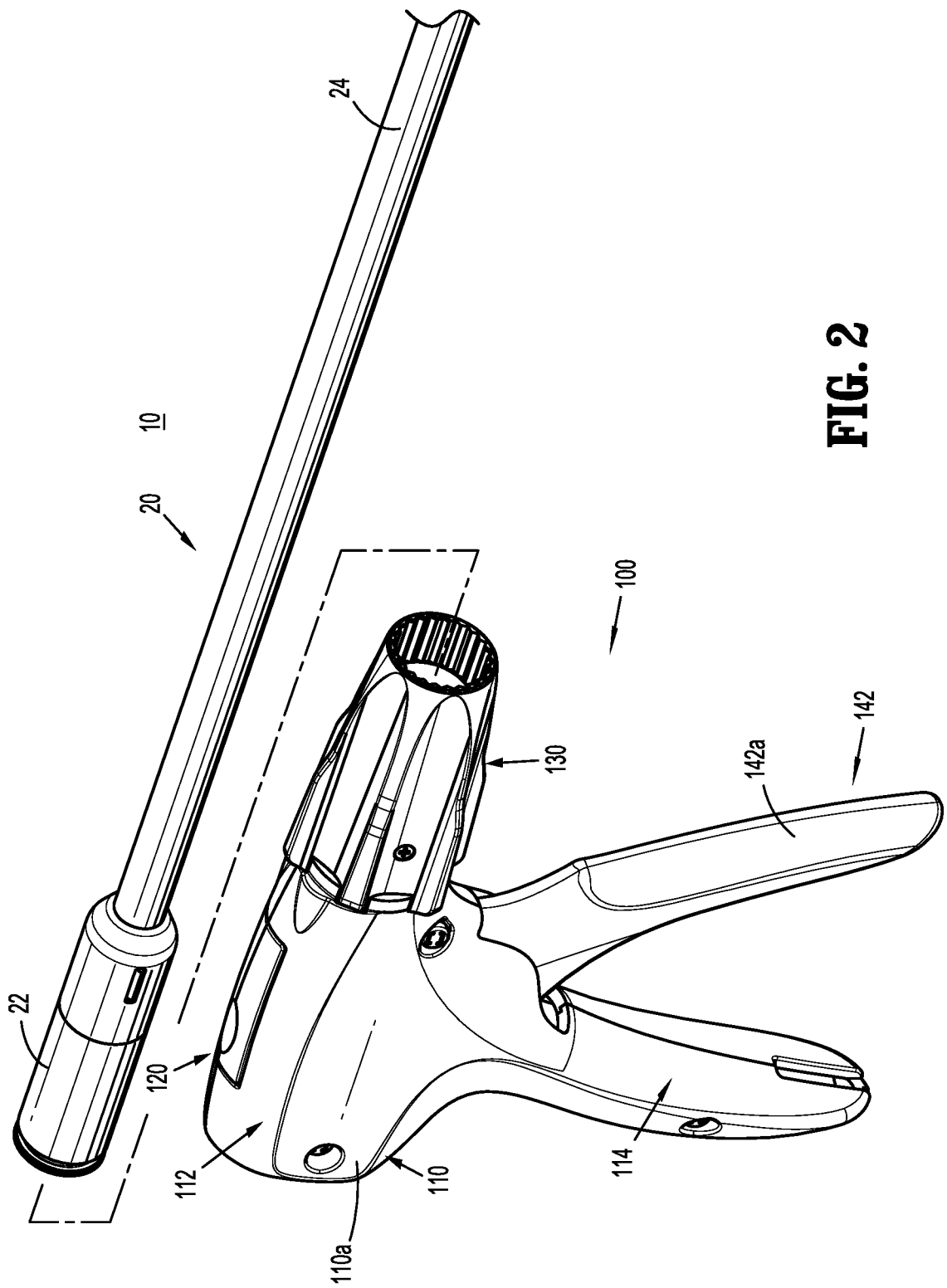
FIG. 2 is front perspective view of the surgical instrument with the elongated assembly removed from the handle assembly.

Turning to FIGS. 1 and 2, a surgical instrument according to aspects of the present disclosure is shown generally as surgical instrument 10. The surgical instrument 10 generally includes a handle assembly 100 and an adapter assembly 20 selectively connectable to the handle assembly 100. The handle assembly 100 is configured to operate the adapter assembly 20 upon connection of the adapter assembly 20 to the handle assembly 100, and may be configured as a sterilizable, reusable component such that handle assembly 100 may be repeatedly used with different and/or additional elongated assemblies (not shown) during the course of one or more surgical procedures. The adapter assembly 20 may be configured as a single-use disposable component, limited-use disposable components, or reusable components, depending upon a particular purpose and/or the configuration of the particular adapter assembly. In either configuration, the need for multiple handle assemblies 100 is obviated and, instead, the surgeon need only select an appropriate adapter assembly, and connect that adapter assembly to the handle assembly 100 in preparation for use.

Figure 3:
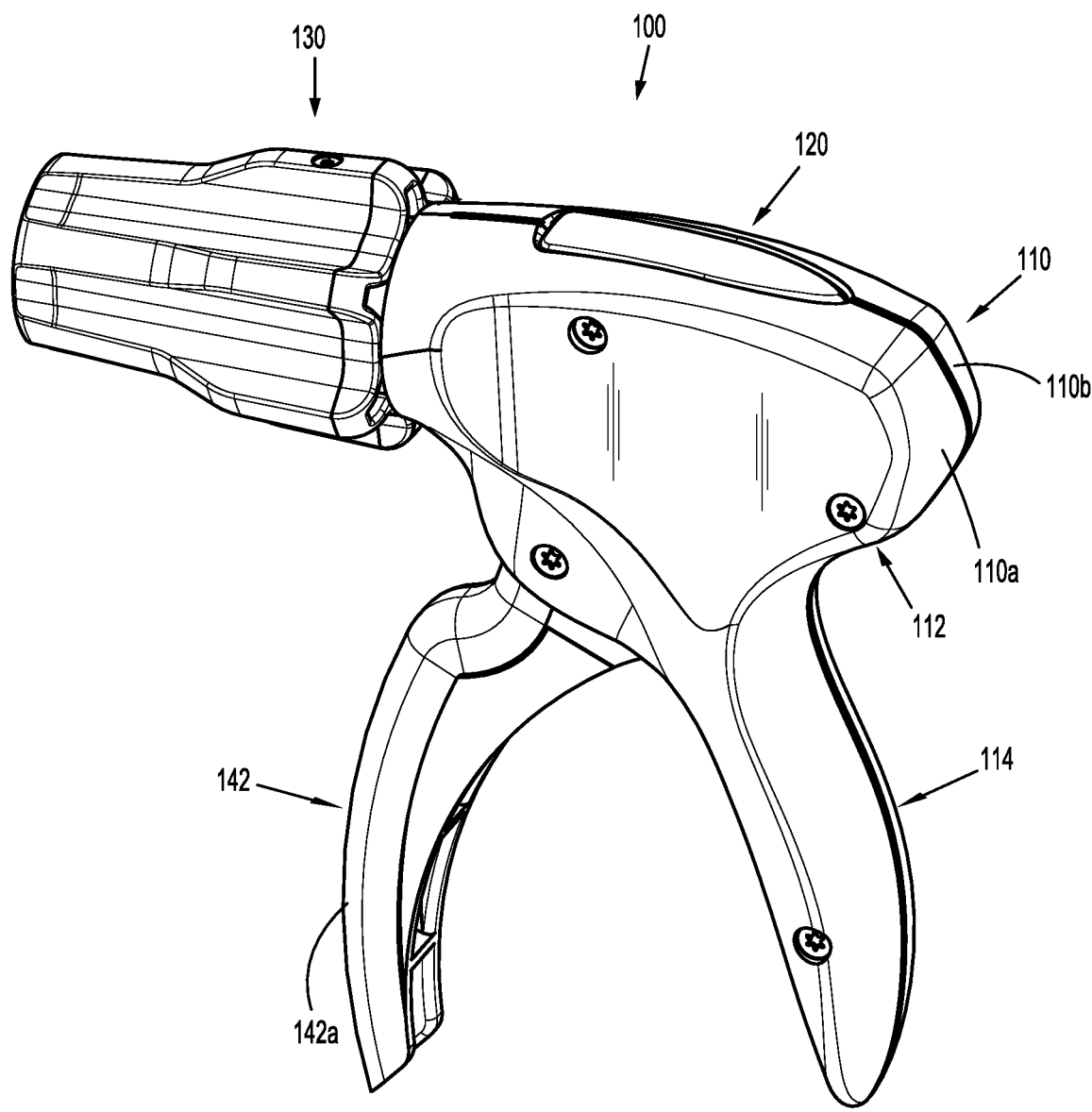
FIG. 3 is a back perspective view of the handle assembly of the surgical instrument shown in FIGS. 1 and 2.
Figure 4:
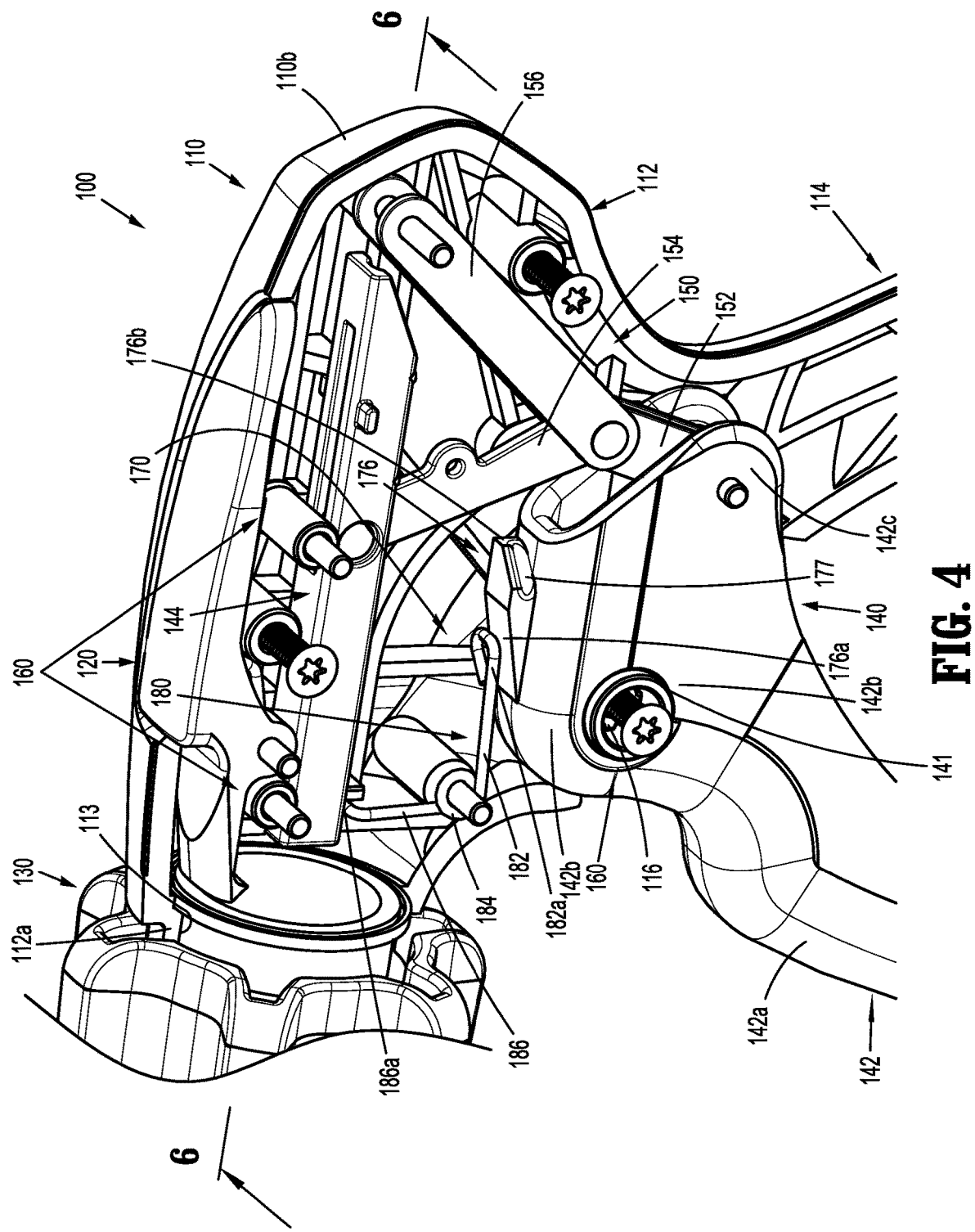
FIG. 4 is a side perspective view of the handle assembly of the surgical instrument shown in FIGS. 1 and 2, with a housing half removed exposing an actuation assembly including a trigger and a linkage assembly.

With additional reference to FIGS. 3 and 4, the handle assembly 100 includes a housing 110, a latch assembly 120 (FIG. 3) operably disposed within housing 110, a rotation knob assembly 130 disposed on a distal end of the housing 110, and an actuation mechanism 140 operably disposed within the housing 110. The housing 110 supports and/or encloses the operating components of handle assembly 100. The latch mechanism 120 is configured to facilitate releasable locking engagement of the adapter assembly 20 with the handle assembly 100. The rotation knob assembly 130 enables the selective rotation of the attached adapter assembly 20 relative to the housing 110. The actuation mechanism 140 is configured to enable selective firing of one or more fasteners (e.g., surgical clips, not shown) from an end effector (not shown) of the attached adapter assembly 20.

The handle assembly 100 will only be described to the extent necessary to fully disclose the aspects of the present disclosure. For a detailed description of the operation and function of an exemplary handle assembly, including exemplary latch and rotation knob assemblies, please refer to commonly owned U.S. Prov. Pat. App. Ser. No. 62/581,144 ("the '144 application"), filed Nov. 3, 2017, the content of which is incorporated herein by reference in its entirety. Other exemplary embodiments of handle assemblies may be found in commonly owned Intl. Pat. App. Nos. PCT/CN2016/096666 and PCT/CN2016/071178, filed on Aug. 26, 2016 and Jan. 18, 2016, respectively, the content of each is hereby incorporated herein by reference in their entireties.

With continued reference to FIGS. 1 and 2, the adapter assembly 20 of the surgical instrument 10 generally includes a proximal hub 22, an elongated shaft 24 extending distally from the proximal hub 22, an end effector (not shown) disposed towards a distal end portion of the elongated shaft 24, and an inner drive assembly (not shown) operably coupled between the handle assembly 100 and the end effector when adapter assembly 20 is engaged with the handle assembly 100, to enable the sequential firing of at least one surgical clip (not shown) about tissue. The end effector of the adapter assembly 20 may be configured to fire surgical clips similar to those shown and described in U.S. Pat. Nos. 7,819,886 or 7,905,890, the contents of each of which are hereby incorporated herein by reference in their entirety.

With additional reference to FIGS. 3 and 4, the housing 110 of the handle assembly 100 may be formed from first and second housing halves 110a, 110b that cooperate to define a body portion 112 and a fixed handle portion 114 depending from the body portion 112. The body portion 112 of the housing 110 includes a distal nose 112a (FIG. 4) defining a distal opening 113 (FIG. 3) therethrough. A proximal end portion of the proximal hub 22 of the adapter assembly 20 is configured to extend at least partially through the distal opening 113 of the distal nose 112a of the housing 110 when the adapter assembly 20 is engaged with the handle assembly 100. The body portion 112 of housing 110 includes a pivot post 116 (FIG. 5) extending transversely within body portion 112.

The actuation mechanism 140 is operably supported by the housing 110 and includes a trigger member 142, a drive member or plunger 144 operably connected to the drive member 144 by a linkage assembly 150, friction reducing mechanisms 160, and a feedback mechanism 170. The friction reducing mechanisms 160 reduce the friction in the handle assembly 100, e.g., between the pivot post 116 and the trigger member 142 and/or between the drive member 144 and the housing 110, thereby providing a smoother firing sequence and a better mechanical advantage.

With particular reference to FIG. 4, the trigger member 142 of the actuation mechanism 140 includes a grasping portion 142a, an intermediate pivot portion 142b, and a proximal extension 142c.

The grasping portion 142a of the trigger member 142 extends downwardly from the body portion 112 of the housing 110 in opposed relation relative to the fixed handle portion 114 of the housing 110. The grasping portion 142a is configured to facilitate grasping and manipulation of the trigger member 142.

Figure 9:
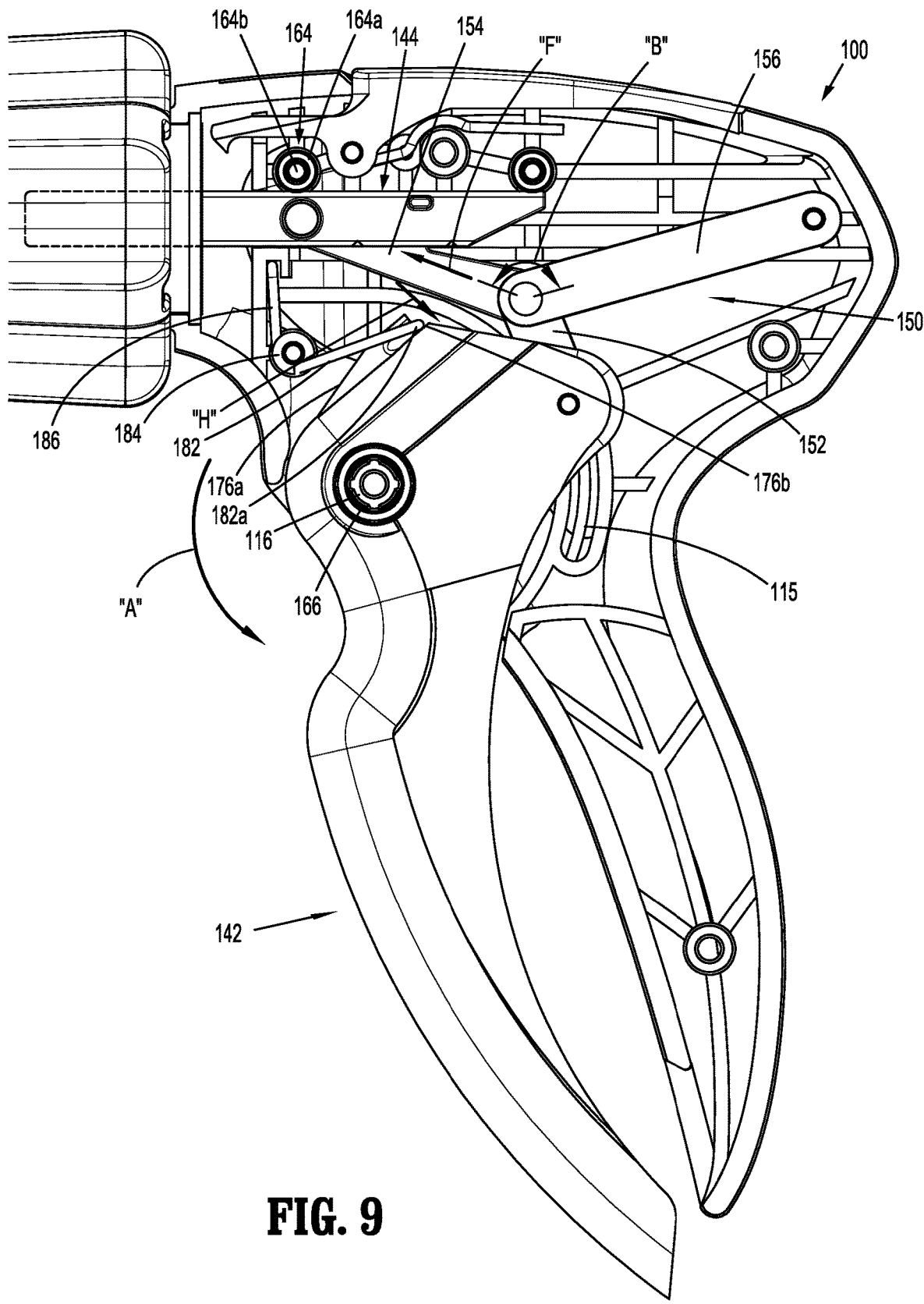
FIG. 9 is a side view of the handle assembly shown in FIG. 4, with the actuation mechanism in an advanced position.

The intermediate pivot portion 142b of the trigger member 142 is at least partially disposed within the housing 110. The intermediate pivot portion 142b defines a pivot aperture 141 configured to receive a third bearing member 166 of the friction reducing mechanisms 160 and the pivot post 116 of the housing 110 received through the third bearing member 166. The third bearing member 166 enables smoother pivoting with less wear of the trigger member 142 about the pivot post 116 and relative to the housing 110 between an initial or pre-actuated position (FIG. 6) and an actuated position (FIG. 9). The grasping portion 142a of the trigger member 142 is spaced-apart from the fixed handle portion 114 when the trigger member 142 is in the initial position, and the grasping portion 142a of the trigger member 142 is approximated to the fixed handle portion 114 as the trigger member 142 is pivoted to the actuated position (FIG. 9).

The proximal extension 142c of the trigger member 142 is disposed on an opposite side of the intermediate pivot portion 142b of the trigger member 142 and, thus, opposite the pivot post 116, as compared to the grasping portion 142a of the trigger member 142. As such, pivoting of the grasping portion 142a to rotate in a first direction, e.g., proximally towards the fixed handle portion 114, pivots the proximal extension 142c to rotate in a second, opposite direction, e.g., distally.

Figure 5:
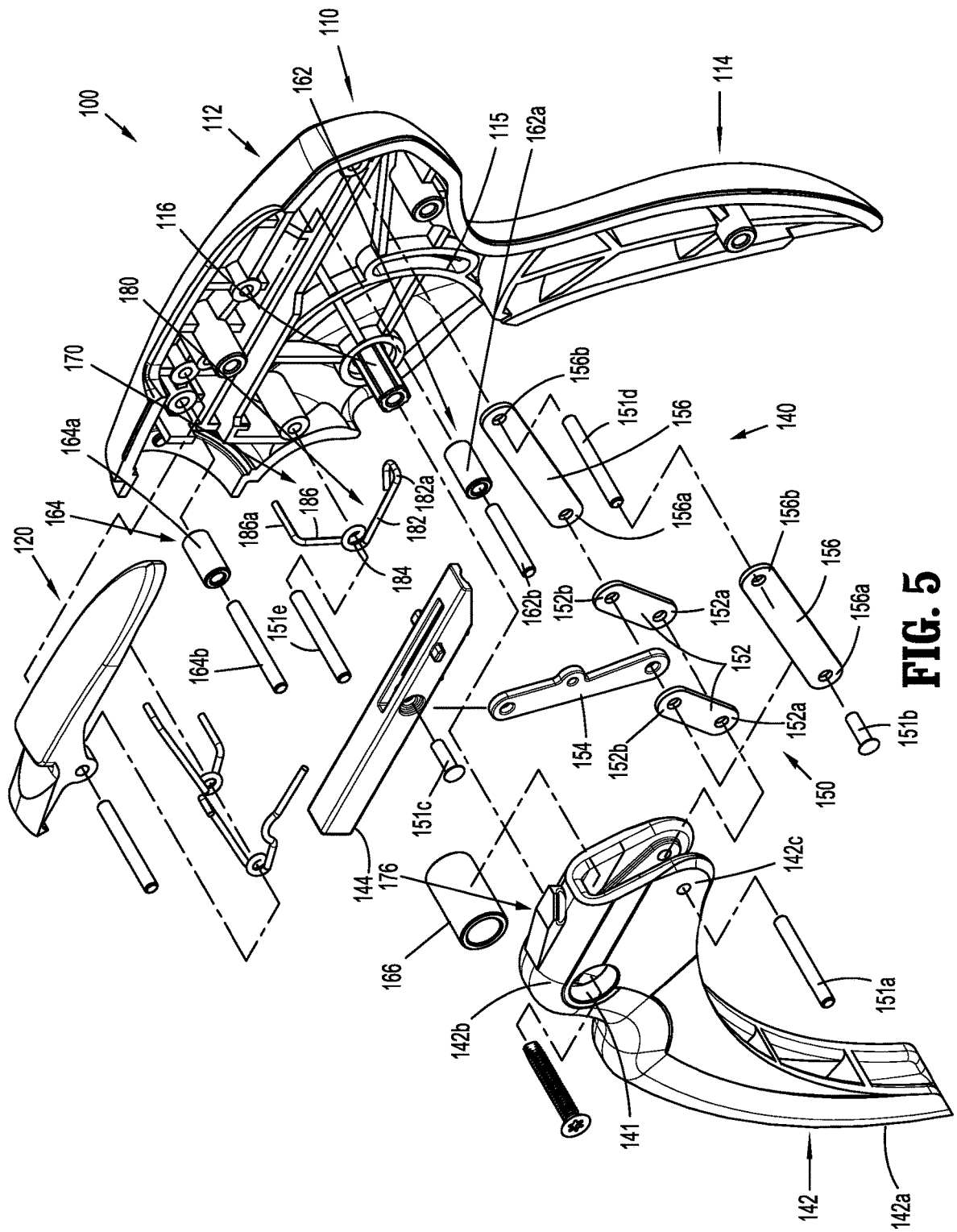
FIG. 5 is an exploded view of the handle assembly shown in FIG. 4.

With addition reference to FIG. 5, the linkage assembly 150 includes a first linkage member or trigger link 152, a second linkage member or plunger link 154, and a third linkage member or fixed link 156. In embodiments, and as shown, the first and third linkage members 152, 156 each include a pair of linkage members 152, 156, although either or both may include only a single linkage member. The first linkage members 152 are pivotally coupled to the proximal extension 142c of the trigger member 142 at first ends 152a of the first linkage members 152 by a first pivot pin 151a. The first pivot pin 151a extends into a track 115 defined in the body portion 112 of the housing 110. The track 115 guides the pivoting of the trigger member 142 during actuation of the handle assembly 100.

The second and third linkage members 154, 156 are each pivotally coupled to second ends 152b of the first linkage member 152 at first ends 154a, 156a of the respective second and third linkages 154, 156 by a second pivot pin 151b. A second end 154b of the second linkage member 154 is pivotally coupled to the drive member 144 by a third pivot pin 151c, while second ends 156b of the third linkage members 156 are pivotally coupled to the body portion 112 of the housing 110 by a fourth pivot pin 151d. The pivot point between the first linkage members 152 and the proximal extension 142c of the trigger member 142, the pivot point between the first linkage members 152 and second and third linkage members 164, 166, and the pivot point between the second linkage member 154 and the drive member 144 are movable pivot points (e.g., movable relative to the housing 110), while the pivot point between the third linkage member 156 and the housing 110 is a fixed pivot point (e.g., fixed relative to the housing 110).

Figure 6:
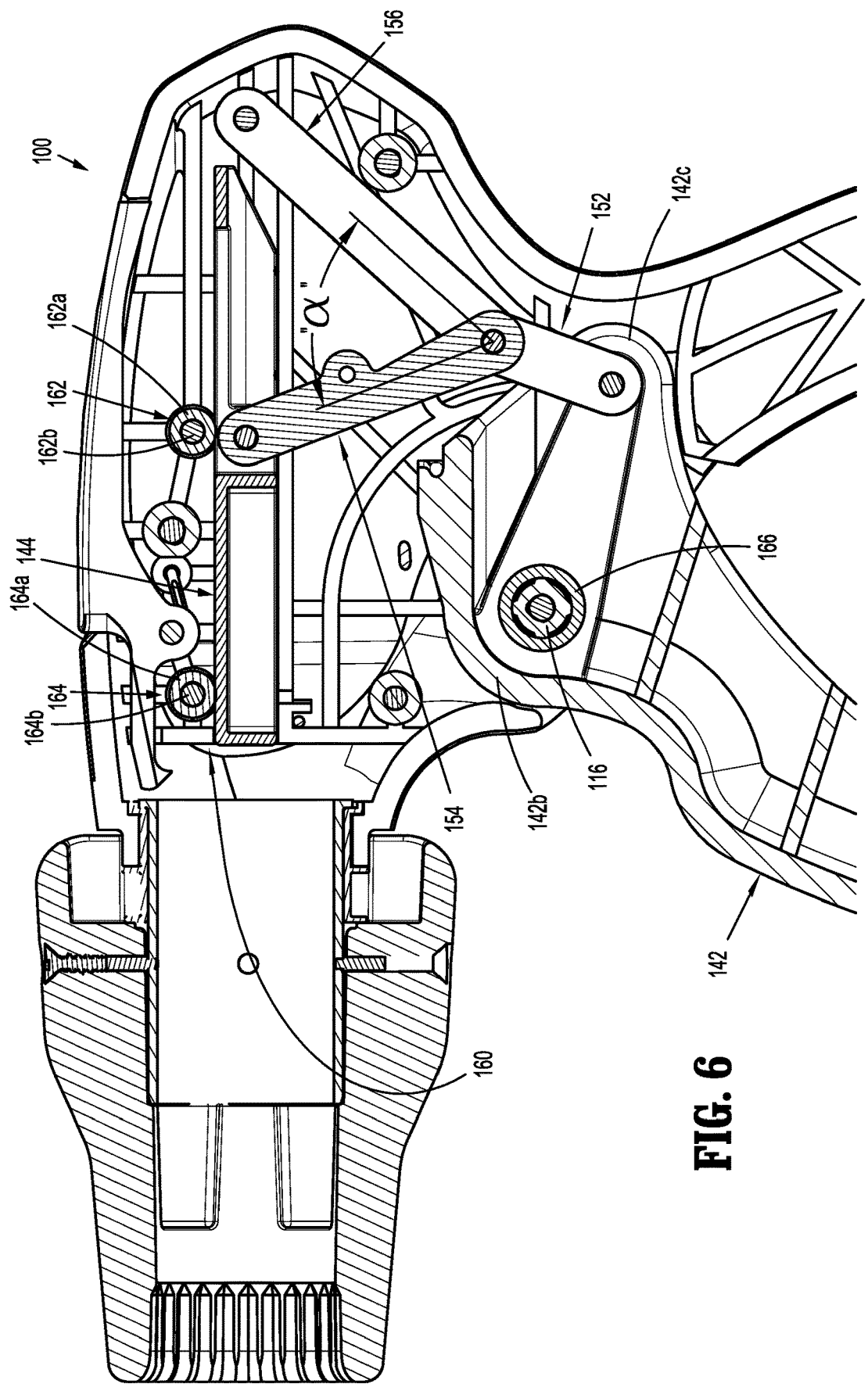
FIG. 6 is a cross-sectional side view taken along line 6-6 shown in FIG. 4.

With reference to FIG. 6, when the linkage assembly 150 of the actuation mechanism 140 is in a first or initial position, the second and third linkage members 154, 156 of the linkage assembly 150 define an angle "α" therebetween less than ninety degrees (90°). The angle "α" is determined to maximize the mechanical advantage of the linkage assembly 150.

Figure 8:
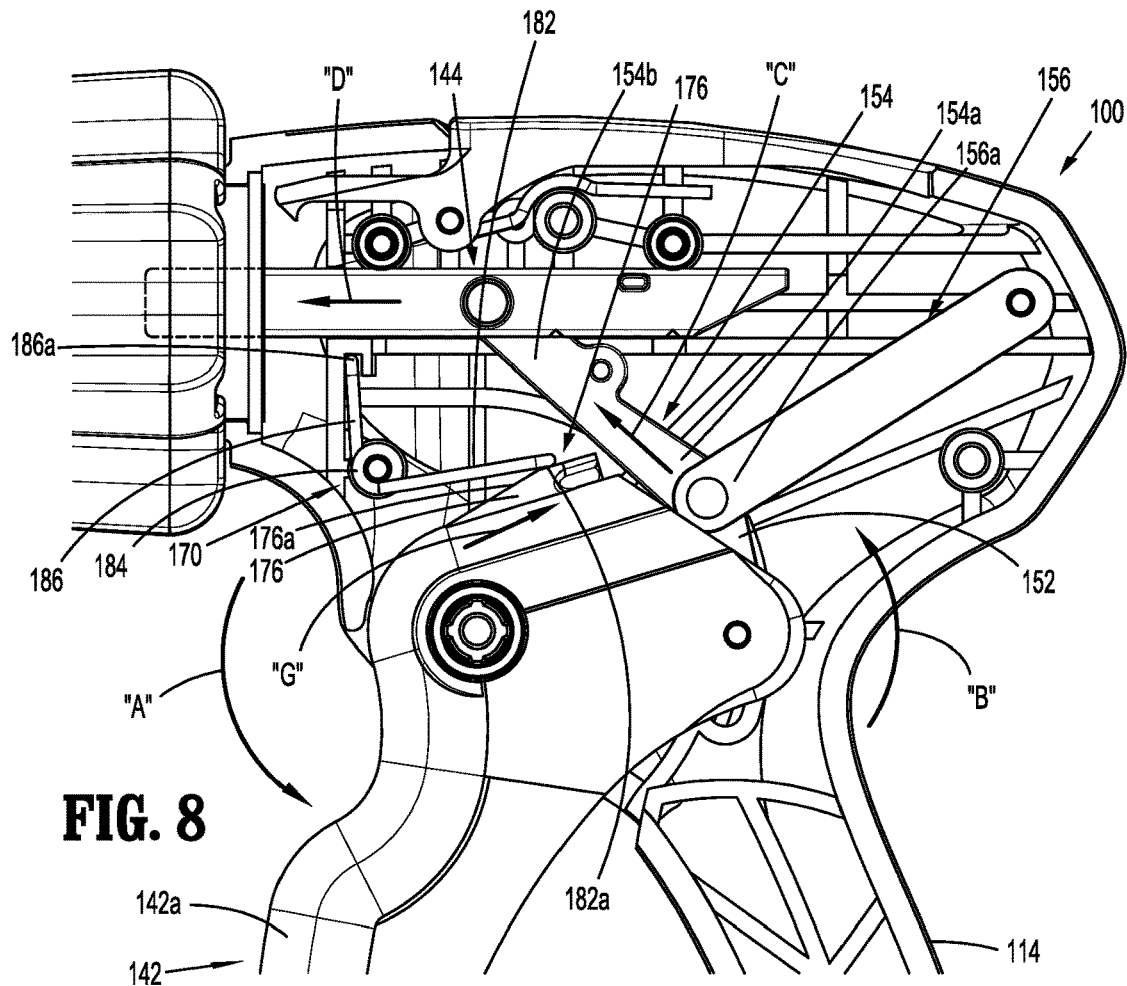
FIG. 8 is a side view of the handle assembly shown in FIG. 4, with the actuation mechanism in a partially advanced position.

With reference to FIGS. 8 and 9, upon actuation of the trigger member 142, e.g., proximal pivoting of the grasping portion 142a of the trigger member 142, as indicated by arrow "A", the proximal extension 142c of the trigger member 142 is moved in a counter-clockwise direction, thereby urging the first linkage member 152 towards the drive member 144. This movement of the first linkage member 152 towards the drive member 144, in turn, urges the first ends 154a, 156a of the second and third linkage members 154, 156, respectively, towards the drive member 144, as indicated by arrow "C" in FIG. 8, to, in turn, urge the second end 154b of the second linkage member 154 distally such that the drive member 144 is translated distally through the body portion 112 of the housing 110, as indicated by arrow "D" shown in FIG. 8. A biasing spring (not shown) may be provided to bias the trigger member 142 towards an initial or pre-actuated position, thereby biasing the drive member 144 proximally.

The drive member 144 of the actuation mechanism 140 is slidably disposed within the body portion 112 of the housing 110 in longitudinal alignment with the adapter assembly 20 when the adapter assembly 20 is engaged with the handle assembly 100. Distal sliding of the drive member 144 through the body portion 112 of the housing 110 during the firing stroke of the handle assembly 100 urges the drive member 144 into contact with a proximal portion (not shown) of inner drive sleeve (not shown) of the elongate assembly 20 to translate the inner drive sleeve distally, e.g., to apply, form or close a surgical fastener or clip supported on an end effector (not shown). In embodiments, a stroke of the drive member 144 is one inch (1") in length.

With continued reference to FIG. 9, when the actuation mechanism 140 is in a fully-actuated position, the second and third linkage members 154, 156 define an angle "β" therebetween greater than ninety degrees (90°). The angle "β" is determined to maximize the mechanical advantage of the linkage assembly 150.

In embodiments, the linkage assembly 150 provides a firing stroke necessary for performing a given function while maximizing an output force. The linkage assembly 150 is designed so a mechanical advantage (and therefore output force) increases smoothly throughout the firing stroke, allowing a user to input a same amount of force while the linkage assembly 150 creates a greater output force at an end of the firing stroke.

With reference back to FIG. 6, the friction reducing mechanisms 160 of the actuation mechanism 140 include first and second sleeve bearing assemblies 162, 164, and the third sleeve bearing 166. The first and second sleeve bearing assemblies 162, 164 include respective first and second sleeve bearings 162a, 164a supported by respective first and second bearing pins 162b, 164b within the body portion 112 of the housing 110. The first and second bearing assemblies 162, 164 of the friction reducing mechanism 160 facilitate distal movement of the drive member 144. More particularly, the first and second sleeve bearings 162a, 164a are rotatably supported about the respective first and second bearing pins 162b, 164b and are positioned to engage the drive member 144. As the drive member 144 slides in a distal direction, the first and second sleeve bearings 162a, 164a rotate about the respective first and second bearing pins 162b, 164b thereby reducing the friction between the body portion 112 of the housing 110 and the drive member 144.

Figure 7:
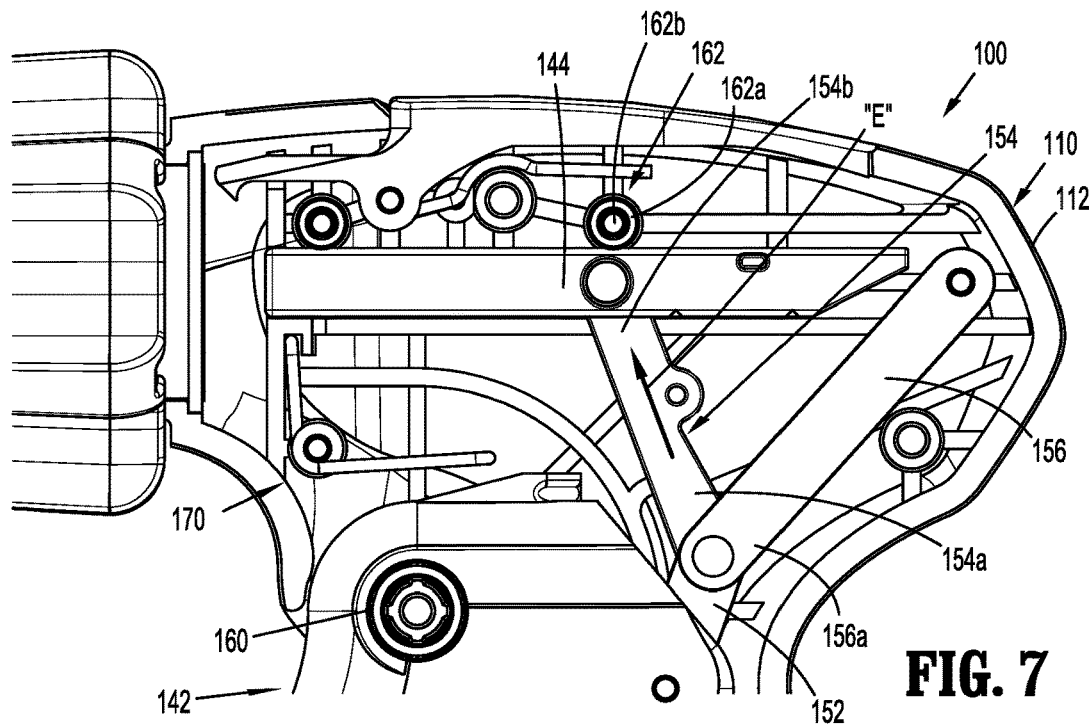
FIG. 7 is a side view of the handle assembly shown in FIG. 4, with the actuation mechanism in an initial position.

In embodiments, the first sleeve bearing assembly 162 is positioned to facilitate initial movement of the linkage assembly 150. More particularly, the first sleeve bearing assembly 162 is positioned such that an initial force output from the second linkage member 154, as indicated by arrow "E" shown in FIG. 7, is tangent to the first sleeve bearing 162a. In this manner, the position of the first sleeve bearing assembly 162 facilitates initial rolling of the first sleeve bearing 162a. The second sleeve bearing assembly 164 is positioned such that a force output from the second linkage member 154, as indicated by arrow "F" shown in FIG. 9, is tangent to the second sleeve bearing 164a at the end of the firing cycle. The first sleeve bearing assembly 162 experiences a higher load at the beginning of the firing stroke and the second bearing assembly 164 experiences a higher load at the end of the firing stroke.

In embodiments, the first and second sleeve bearings 162, 164 are formed of polyether ether ketone (PEEK), nylon, other polymers, metal, or other suitable material.

Although shown as having only the first and second sleeve bearing assemblies 162, 164 supporting the drive member 144, it is envisioned that the friction reducing mechanism 160 may include more than two sleeve bearing (not shown).

As noted above, the third sleeve bearing 166 of the friction reducing mechanism is received about the pivot post 116 of the body portion 112 of the housing 110. The intermediate pivot portion 142b of the trigger member 142 of the actuation mechanism 140 defines the pivot aperture 141 that receives the pivot post 116 of the housing 110. The third sleeve bearing 166 of the friction reducing mechanism 160 is disposed within the pivot aperture 141 in the trigger member 142 such that the third sleeve bearing 166 is positioned between the pivot post 116 of the body portion 112 and the trigger member 142.

In embodiments, the third sleeve bearing 166 is fixed relative to the pivot post 116 such that the trigger member 142 of the actuation mechanism 140 rotates relative to the third bearing sleeve 166 and the pivot post 116. In other embodiments, the third bearing sleeve 166 is fixed relative to the trigger member 142 such that the trigger member 142 and the third sleeve bearing 166 rotate relative to the pivot post 116. In yet other embodiments, the third sleeve bearing 166 is neither fixed relative to the pivot post 116 nor fixed relative to the trigger member 142. In this manner, the third sleeve bearing 166 rotates relative to either or both of the pivot post 116 and the trigger member 142.

In embodiments, the third sleeve bearing 166 is formed of stainless steel, PEEK, or other suitable material. The third sleeve bearing 166 reduces friction between the trigger member 142 and the body portion 112 of the housing 110, thereby reducing wear in the handle assembly 100.

The actuation mechanism 140 further includes the feedback mechanism 170 for signal, e.g., audible or tactile, completion of a firing stroke. As described below, the feedback mechanism 170 produces an audible and/or or tactile feedback during actuation of the handle assembly 100 upon completion of an actuation stroke, e.g., full clip formation.

With particular reference to FIG. 4, the feedback mechanism 170 is operably disposed within the body portion 112 of the housing 110 of the handle assembly 100 and includes a ramp portion 176 and a torsion spring 180. More particularly, the ramp portion 176 is formed on an outer surface of the intermediate pivot portion 142b of the trigger member 142 of the actuation mechanism 140. The ramp portion 176 includes an inclined surface 176a and an edge surface 176b, and defines a cam track 177. As will be detailed below, during a firing stroke of the handle assembly 100, the ramp portion 176 directs a hammer portion 182a of the torsion spring 180 into a snapping engagement with an outer surface of the intermediate pivot portion 142b of the trigger member 142 to provide an audible and/or tactile response that the handle assembly 100 firing stroke is complete, e.g., the actuation mechanism 140 is fully actuated. The ramp portion 176 is configured to reset the hammer portion 182a of the torsion spring 180 as the trigger member 142 returns to its pre-actuated position to permit subsequent firing of the handle assembly 100.

The torsion spring 180 includes an elongate body 182 with the hammer portion 182a disposed on a first, free end and a spring portion 184 on a second end. A flange portion 186 extends from the spring portion 184 and includes an engagement portion 186a formed on a free end of the flange portion 186.

The spring portion 184 of the torsion spring 180 of the feedback mechanism 170 is received by a fifth pivot pin 151e that is supported within the body portion 112 of the housing 110. The elongate portion 182 of the torsion spring 180 extends towards the intermediate pivot portion 142b of the trigger member 142 such that the hammer portion 182a of the torsion spring 180 engages the inclined portion 176a of the ramp portion 176 of the feedback mechanism 170. The engagement portion 186a of the torsion spring 180 engages the body portion 112 of the housing 110 and remains in a fixed position.

With particular reference to FIG. 8, upon actuation of the trigger member 142, e.g., proximal pivoting of the grasping portion 142a of the trigger member 142 toward the fixed handle portion 114 of the housing 110, as indicated by arrow "A", the intermediate pivot portion 242b of the trigger member 142 moves in a counter-clockwise direction, as indicated by arrow "B". The counter-clockwise movement of the intermediate pivot portion 142b of the trigger member 142 causes the hammer portion 182a on the free end of the elongate body 182 of the torsion spring 180 to ride along the inclined surface 176a of the ramp portion 176 of the feedback mechanism 170, as indicated by arrow "G" shown in FIG. 8.

During actuation of the trigger member 142, the engagement portion 186a on the free end of the flange portion 186 of the torsion spring 180 remains in a fixed position. The movement of the hammer portion 182a of the torsion spring 180 along the inclined surface 176a of the ramp portion 176 cams the spring portion 184 of the torsion spring 180 to a loaded condition.

Turning to FIG. 9, the ramp portion 176 and the torsion spring 180 of the feedback mechanism 170 are configured such that at the end of the actuation stroke, the hammer portion 182a of the torsion spring 180 disengages from the edge surface 176b of the ramp portion 176. As noted above, during actuation of the trigger member 142, the spring portion 184 is cammed to the loaded condition. In this manner, when the hammer portion 182a of the torsion spring 180 disengages from the edge surface 176b of the ramp 176, the hammer portion 182a snaps against the outer surface of the intermediate pivot portion 142b of the trigger member 142, as indicated by arrow "H", thereby producing an audible response. It is envisioned that the contact of the hammer portion 182a of the torsion spring 180 may also produce a tactile response, e.g., vibration.

As the trigger member 142 returns to its initial position, the elongate body 182 of the torsion spring 180 advances relative to the ramp portion 176 such that the hammer portion 182a of the torsion spring 180 engages the cam track 167 of the ramp portion 176. As the hammer portion 182a engages the cam track 167 of the ramp portion 176, the hammer portion 182a is guided around the ramp portion 176 to return to the hammer portion 182a to its initial position disposed along the inclined surface 176a of the ramp portion 176, thereby resetting the feedback mechanism 170, and readying the handle assembly 100 for further use.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:
1. A handle assembly, comprising:
a housing defining a longitudinal axis;
a trigger operably coupled to the housing and movable to cause actuation of the handle assembly;

a drive member movable within the housing from an initial position to an advanced position in response to actuation of the trigger; and a linkage assembly operably disposed between the trigger and the drive member to move the drive member from the initial position to the advanced position, the linkage assembly including first, second, and third linkage members, the first linkage member being pivotally secured to the trigger on a first end and to first ends of the second and third linkage members on a second end, the second linkage member being pivotally secured to the drive member on a second end, and the third linkage member being pivotally secured to the housing on a second end, wherein the second and third linkage members each define a longitudinal axis, the longitudinal axis of the second linkage member forming an angle of less than ninety degrees with the longitudinal axis of the third linkage member when the drive member is in the initial position.

2. The handle assembly of claim 1, wherein the first and third linkage members each include a pair of linkage members.

3. The handle assembly of claim 1, wherein the first end of the first linkage member is pivotally secured to the trigger by a first pivot pin.

4. The handle assembly of claim 3, wherein the housing defines a track and the first pivot pin extends within the track.

5. The handle assembly of claim 1, wherein the housing includes a body portion and a trigger portion.

6. The handle assembly of claim 1, further including a friction reducing mechanism operably disposed within the housing relative to the drive member.

7. The handle assembly of claim 6, wherein the friction reducing mechanism includes first and second bearing assemblies, each of the bearing assemblies including a sleeve rotatably disposed within the housing and configured to facilitate movement of the drive member.

8. The handle assembly of claim 7, wherein the first bearing assembly is positioned such that a longitudinal axis of the second linkage member is tangent to the first bearing sleeve when the linkage assembly is in an initial condition.

9. The handle assembly of claim 8, wherein the second bearing assembly is positioned such that the longitudinal axis of the second linkage member is tangent to the second bearing sleeve when the linkage assembly is in a fully-actuated condition.

10. The handle assembly of claim 7, wherein the first bearing assembly includes a first pivot pin and the second bearing assembly includes a second pivot pin, the first and second bearing sleeves being rotatably supported about the respective first and second pivot pins.

11. The handle assembly of claim 6, wherein the housing includes a pivot post and the friction reducing mechanism includes a bearing sleeve, the bearing sleeve being received about the pivot post between the pivot post and the trigger to reduce friction between the housing and the trigger during actuation of the handle assembly.

12. The handle assembly of claim 1, wherein the second and third linkage members define a second angle therebetween when the drive member is in the advanced position.

13. The handle assembly of claim 12, wherein the second angle is greater than ninety degrees.

14. The handle assembly of claim 1, further including a feedback mechanism disposed within the housing to indicate when the drive member attains the advanced position.

15. A handle assembly, comprising:

a housing defining a longitudinal axis and a track;

a trigger operably coupled to the housing and movable to cause actuation of the handle assembly;

a drive member movable within the housing from an initial position to an advanced position in response to actuation of the trigger; and a linkage assembly operably disposed between the trigger and the drive member to move the drive member from the initial position to the advanced position, the linkage assembly including first, second, and third linkage members, the first linkage member being pivotally secured by a first pivot pin to the trigger on a first end and to first ends of the second and third linkage members on a second end, the first pivot pin extends within the track, the second linkage member being pivotally secured to the drive member on a second end, and the third linkage member being pivotally secured to the housing on a second end.

16. The handle assembly of claim 15, wherein the first and third linkage members each include a pair of linkage members.

17. The handle assembly of claim 15, wherein the housing includes a body portion and a trigger portion.

18. The handle assembly of claim 15, further including a friction reducing mechanism operably disposed within the housing relative to the drive member.

* * * * *